United States Patent [19]
Matsushita et al.

[11] Patent Number: 6,027,485
[45] Date of Patent: *Feb. 22, 2000

[54] RETAINING FASTENER AND DIAPER USING THE FASTENER

[75] Inventors: Michiyo Matsushita, Ehime; Akiko Hirano; Ikuo Akiyama, both of Kagawa, all of Japan

[73] Assignee: Uni-Charm Corporation, Ehime, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/856,361

[22] Filed: May 14, 1997

[30] Foreign Application Priority Data

May 24, 1996 [JP] Japan ..................... 8-129738

[51] Int. Cl.$^7$ ........................................ A61F 13/15
[52] U.S. Cl. .............................. 604/391; 2/912; 24/442; 604/387
[58] Field of Search .................... 604/387, 391; 2/912, 920; 24/442, 444–447, 449–452

[56] References Cited

U.S. PATENT DOCUMENTS

| | | | |
|---|---|---|---|
| 3,748,701 | 7/1973 | De Mestral | 24/204 |
| 5,032,122 | 7/1991 | Noel et al. | 604/391 |
| 5,611,791 | 3/1997 | Gorman et al. | 604/391 |
| 5,624,427 | 4/1997 | Bergman et al. | 604/391 |
| 5,647,864 | 7/1997 | Allen et al. | 604/391 |
| 5,735,840 | 4/1998 | Kline et al. | 604/391 |

FOREIGN PATENT DOCUMENTS

| | | |
|---|---|---|
| H4-56008 | 5/1992 | Japan . |
| H6-507800 | 9/1994 | Japan . |
| WO92/20251 | 11/1992 | WIPO . |

*Primary Examiner*—John G. Weiss
*Assistant Examiner*—Dennis Ruhl
*Attorney, Agent, or Firm*—Koda & Androlia

[57] ABSTRACT

Medium members such as thread are provided between woven fabric sheet such as warp knitting serving as the other sheet and base member, forming linear raised portions in the woven fabric sheet. The density of woven fabric sheet at the inclined portions to either side of these raised portions becomes coarse and the gaps between fine filaments on the woven fabric sheet spread, so that retaining heads of one sheet can easily enter and so that the fine filaments easily become hooked to the base portion of the retaining heads. Consequently, the retaining of the one sheet and the other sheet in strengthened, and the peeling strength is improved.

8 Claims, 4 Drawing Sheets

RETAINING FASTENER AND DIAPER USING THE FASTENER

BACKGROUND OF THE INVENTION

1. Field of the Invention

The present invention relates to a retaining fastener wherein a plurality of protrusions having retaining heads provided to a one sheet are retained to a the other sheet, and to disposable diapers and the like using this retaining fastener; and particularly to a retaining fastener wherein the retaining strength of the one sheet and the other sheet has been improved, and to diapers using this fastener.

2. Description of the Prior Art

Regarding the type of disposable diapers generally referred to as "open-type" diapers, the front part and rear part are formed continuously so as to be foldable in two. In use, the rear part is applied to the baby's rump and the front part is passed across the crotch and applied to the side of the abdomen. Next, wing-like formations on either side of the rear part are retained to an exterior sheet on the front part. As for means for retaining the aforementioned wing-like formations to the surface of the front side, an arrangement using retaining fasteners has been suggested.

As shown in FIG. 7, this retaining fastener is comprised of a one sheet 1 and an other sheet 2. The one sheet 1 is formed of a resin material, and is comprised of a base sheet 1a and protrusions 3 arrayed in order over the entire surface of this base sheet 1a, with retaining heads 3a being integrally formed on the tip of these protrusions 3. The overall form of the protrusion 3 and the retaining head 3a is a T-shaped or J-shaped form. The other sheet 2 is comprised of a plurality of loops 4 of filaments formed on a base material 2a, or the entirety is formed of man-made woven fabric or non-woven fabric, or the like.

What is required of retaining fasteners to be used for disposable diapers and the like is that the item be inexpensive and at the same time be able to exhibit a certain degree of retaining strength; woven fabric or non-woven fabric used as the other sheet is preferably used to satisfy these conditions. Also, it is preferable that the form of the retaining heads 3a of the one sheet 1 be of a T-shaped or mushroom-shaped form so as not to stimulate the skin upon contact.

However, what is most required of a retaining fastener regarding the function thereof is the retaining strength between the one sheet and the other sheet. If the retaining strength is weak, in the event that the retaining fastener is used for diapers, movement of legs may cause the one sheet and the other sheet to become separated one from another, resulting in the front part and rear part of the diaper shifting in position or coming loose from the body of the wearer, thus allowing for possible leakage of waste.

In order to improve this matter, Japanese Utility Model Provisional Publication No. H4-56008 discloses art wherein a fiber with a great many of loop and coil tangles is mixed into non-woven fabric used as the other sheet, thus facilitating easy hooking of the retaining heads of the one sheet to the other sheet. Also, disclosed in International Patent Publication No. WO 92/20251 is art wherein the ratio between the area of the joining portions between fibers of the non-woven fabric used as the other sheet and the area of the joining portions of the non-woven fabric and packing is made to be a ratio within acertain range; thus securing a wide area capable of causing retaining between the other sheet and the retaining heads of the one sheet.

However, even if such known retaining fasteners are used, there is a limit to the extent to which the retaining strength can be raised. There reason thereof is that with retaining fasteners, e.g., as shown in FIG. 7, not necessarily all of the protrusions 3 of the one sheet 1 are retained by the other sheet 2. In other words, since the one sheet 1 and the other sheet 2 are adhered one to another at a generally uniform pressure over the entire area thereof, some of the protrusions 3 only deform in a retracting direction, and thus the retaining heads 3a thereof cannot enter into the loops 4 of the other sheet 2 or opening space (gaps) between fibers of the woven fabric or non-woven fabric, and as a result, the retaining heads 3a and the loops 4 of the other sheet 2 or the fibers do not be hooked enough.

SUMMARY OF THE INVENTION

The present invention has been made in order to solve the problems of the aforementioned known art.

Accordingly, it is an object of the present invention to provide a retaining fastener wherein a region is formed in which the retaining protrusions on the tip of the protrusions of the one sheet are securely retained to the other sheet, thus increasing retaining strength.

It is another object of the present invention to provide a retaining fastener wherein the region in which the one sheet and the other sheet are securely retained can be set to an optimal position and an optimal range, and wherein a desired retaining strength can be set for each product.

It is a further object of the present invention to provide a diaper using the above retaining fastener, wherein wing-like formations on the sides of the rear part are retained to the surface of the front part at optimal retaining strength.

The present invention is a retaining fastener, comprising: one sheet upon which are provided a plurality of protrusions having retaining heads; and the other sheet to which the retaining heads are retained, wherein the aforementioned other sheet is raised toward the aforementioned one sheet in some portions.

In the above, the structure may be arranged to be such that, for example, a linear medium members are provided intermittently provided between the rear side of the other sheet and the base member to which this the other sheet is to be attached, thereby causing the other sheet to rise linearly following the aforementioned medium members partially. It is preferable that the dimensions of rising of the other sheet be set so as to be greater than the height dimensions of the retaining head of the protrusions on the one sheet.

For the one sheet comprising the retaining fastener according to the present invention, such having disk-shaped or mushroom-shaped retaining heads on the tip of the plurality of orderly arrayed protrusions is favorably used. Also, the entirely of the protrusions and the retaining head may be formed as a J-shaped hook form. Further, for the other sheet, woven fabric or non-woven fabric is used. For the woven fabric, a warp knitting such as tricot knitting or etc., may be used. The warp knitting is made of two or more kinds of filaments and it is preferable that at least one of the aforementioned filaments is multifilament which formed of twisting a plurality of fine filaments or many fibers. In the event of the warp knitting made of the multifilaments and other filaments, the multifilaments fluff and thus the fine filaments or many fibers protrude from the multifilaments. In the present invention, it is preferable that many loops of the aforementioned protruding fine filaments are formed on the surface of the other sheet. Although the retaining fastener of the present invention is applicable to a wide variety of products, it is preferable regarding application to disposable diapers that the protrusions and the retaining heads of the one sheet be of a T-shape or mushroom-shape, so a to reduce stimulation to the skin, and that an inexpensive fabric or non-woven fabric be used for the other sheet.

With the present invention, partial raised portions are formed to the aforementioned the other sheet. These raised portions can be easily formed by means of providing linear medium members between the rear side of the other sheet and the base member to which this the other sheet is to be attached. By forming such raised portions in the other sheet, the side portion of the raised portion are at an angle to the direction of pressure of the one sheet, and the density of the other sheet becomes coarse and the gaps between fine filaments (loops) or fibers of the other sheet spread at the aforementioned inclined portions. The density being coarse means that the probability of the retaining heads of the protrusions of the one sheet entering the gaps between the fine filaments or fibers of the other sheet is greatly increased. Also, hooking of the retaining head to the fine filaments or the fiber or loops is facilitated at the aforementioned inclined portions. Accordingly, the one sheet and the other sheet are easily retained at the raised portions of the other sheet. Particularly, the probability of the retaining head engaging with the fine filaments or fibers of the other sheet at the aforementioned inclined portions are increased by making the height dimensions of the raised portion (the difference of thickness of the other sheet under weight of 0.5 g/cm2, for example) of the other sheet to be greater the height dimensions of the retaining head.

Further, the retaining head of the protrusions of the one sheet are retained to the fine filaments or fibers of the other sheet even where the raised portions are not formed, but the overall retaining strength of the retaining fastener is increased by means of raising the probability of hooking at the aforementioned raised inclined portions.

The retaining strength can be increased by making the area on the other sheet at which the aforementioned raised inclined portions are formed to be 3% or more of the entire area of contact of the one sheet and the other sheet. A greater area of the inclined portions on the other sheet increases the retaining strength, but increasing the said area too much causes the absolute area of the aforementioned inclined portions to decrease, thus defeating the purpose of increasing the effects of increased probability of hooking. Accordingly, it is preferable that the upper limit of the aforementioned area ratio be around 50%.

Further, the characteristic of the present invention is in that by appropriately setting the area of the aforementioned raised portions as compared to the total contact area between the one sheet and the other sheet, or more specifically, the area of the inclined portions formed by the raised portions, the retaining strength between the one sheet and the other sheet can be adjusted or set. In other words, the retaining strength can be relatively freely set by selecting the shape and size of the medium members according to the retaining strength required of the products for which the retaining fastener is to be used.

The form of the aforementioned raised portions can be arbitrarily decided, and may be dot or circle shaped raised portions arrayed either orderly or disorderly, but it is preferable that raised portions extending in a linear or straight line manner be formed by providing thread, resin filament, resin rods, or the like between the rear side of the other sheet and the base member. Raised portions extending in a linear or straight line manner result in the inclined portions being extended linearly, thus increasing the probability that the protrusions of the one sheet will come into contact with the inclined portions. Also, thread or the like can be used for the medium members between the other sheet and the base member, thus reducing production costs. Further, the raised portions can be configured such that lines intersect in a cross stripes-like form.

In the event of providing raised portions extending in a linear or straight line manner, it is preferable that the aforementioned raised portions are provided at right angles to the direction in which shearing force acts upon the contact portions between the one sheet and the other sheet. Setting the direction of the raised portions such increases the resisting retaining strength to the shearing or peeling force acting upon the one sheet and the other sheet.

Further, in the event that woven fabric such as warp knitting or the like is used for the other sheet, it is preferable that the direction of extension of the main filaments 13a and the direction of the extension of the raised portion be parallel. Said main filaments comprise multifilaments made of twisting a plurality of the fine filaments (or many fibers), and the great number of the fine filaments 13b of multifilaments extend nearby or alongside of multifilaments. Such an arrangement allows for the retaining heads of the one sheet to easily hook to the gaps between the great number of filaments, thus increasing retaining strength.

Further, the present invention comprises a diaper which has an absorptive portion on the inner side of a covering sheet, with a front part and rear part formed to be foldable in two, wherein the aforementioned retaining fastener is used, and wherein the other sheet of this fastener is provided to the covering sheet of the aforementioned front part, and the one sheet is provided to the wing-like formations which protrude from the sides of the rear part and overlap with the aforementioned front part.

The diaper using the aforementioned retaining fastener is easily applied to and removed from babies or the like, and the retaining fastener does not come loose easily from movement of the body or legs while being worn.

DESCRIPTION OF THE PREFERRED EMBODIMENT

Figure 1:
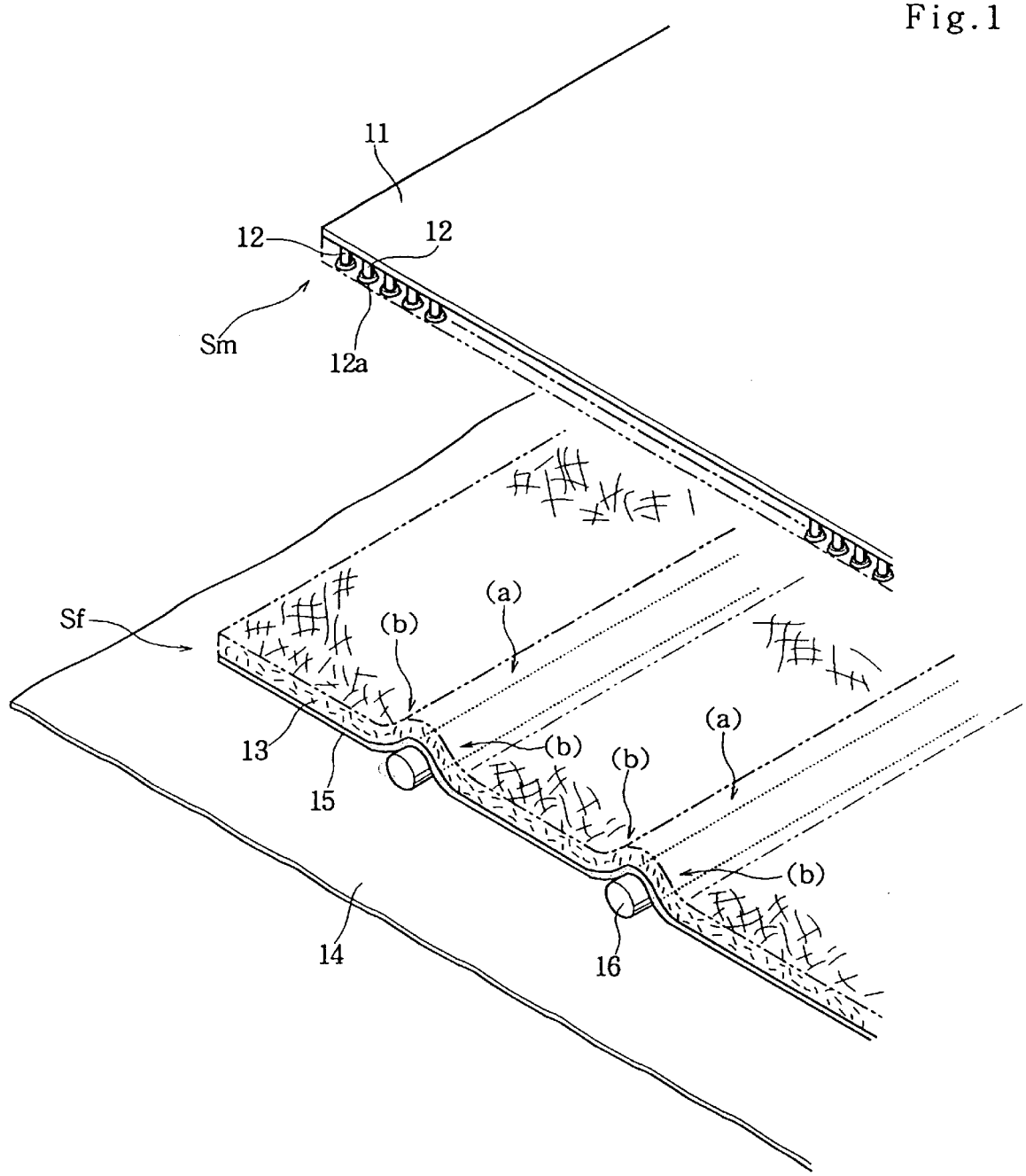
FIG. 1 is a perspective view of the retaining fastener according to the present invention.

As shown in FIG. 1, this retaining fastener is comprised of one sheet Sm and other sheet Sf, wherein the one sheet Sm and the other sheet Sf are capable of being repeatedly mutually peeled and retained.

Figure 2:
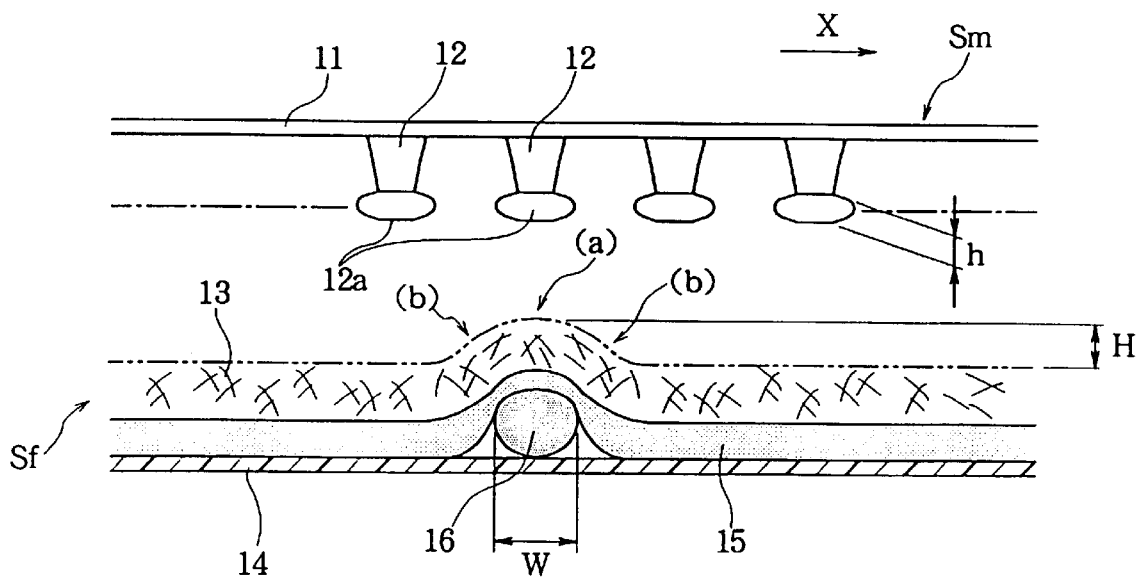
FIG. 2 is a cross-sectional diagram illustrating the one sheet and the other sheet of the retaining fastener.

The one sheet Sm is formed of the like of a resin material of polypropylene (PP) or a mix of polypropylene (PP) and polyethylene (PE). As shown in FIG. 2, a great number of protrusions 12 are orderly arrayed on the base sheet 11 of the one sheet Sm, and a retaining head 12a is formed on the tip of each of the protrusions 12. The retaining head 12a is disk-shaped, and the entirely of the protrusion 12 including the retaining head 12a is of a T-shaped or mushroom-shaped form. The retaining heads 12a are formed by means of heating and deforming the tip portion of the plurality of protrusions 12, or some like manner.

Figure 3:
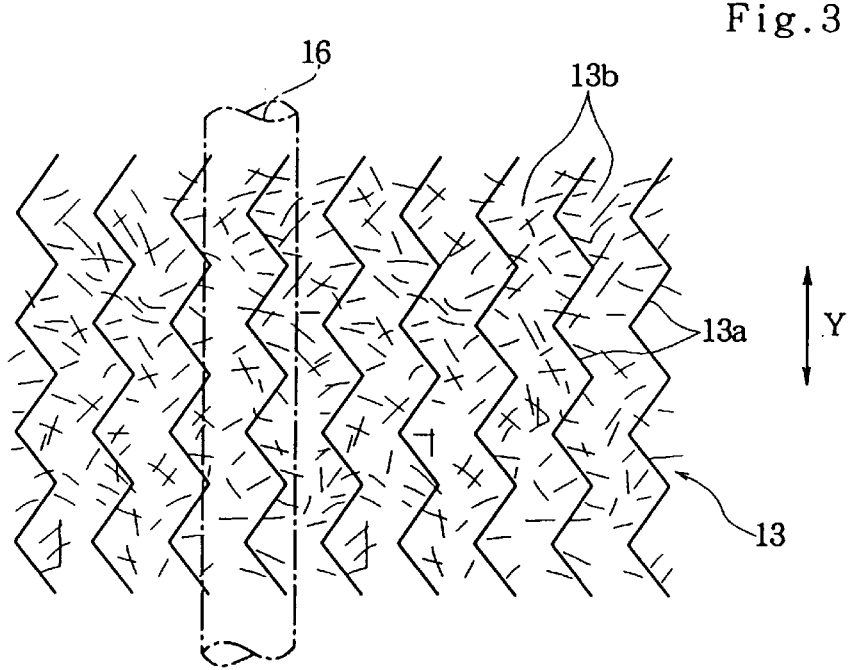
FIG. 3 is an enlarged plan view of the other sheet.

For the other sheet Sf, a woven fabric sheet 13 such as warp-knitting of man-made filaments or fibers is used. As shown in FIG. 3, the aforementioned woven fabric sheet 13 is comprised of main filaments 13a which comprise multifilaments formed of a plurality of fine filaments or many fibers extending in the Y-direction in a zigzag manner(ribbed manner), and a great number of fine filaments 13b provided between the main filaments 13a by main filaments 13a (multifilaments) fluffing. The aforementioned main filaments 13a act to stabilize the fine filaments 13b extending therefrom. This woven fabric sheet 13 is formed by knitting polyester fibers or nylon fibers, and the woven fabric sheet 13 used was that with basic weight of 30 g/m2 to 80 g/m2.

Figure 4:
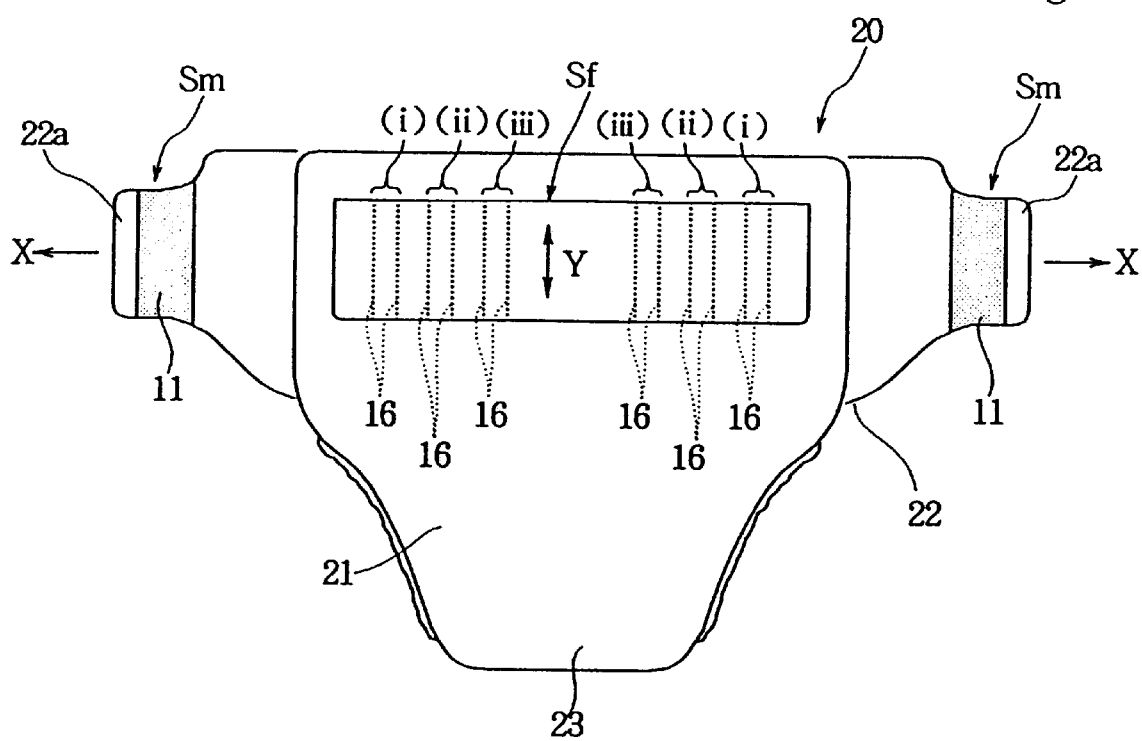
FIG. 4 is a frontal view of a disposable diaper as an example of a product provided the retaining fastener.

The other sheet Sf comprising the aforementioned woven fabric sheet 13 is attached to the base members 14 by means of adhesion. This base members 14 is the surface sheet of the product; in the event that the product is a diaper such as shown in FIG. 4 wherein the retaining fastener is to be attached, the aforementioned fine filaments 14 is the covering sheet formed of a resin film which is water-repellent and porous to air.

The aforementioned woven fabric sheet 13 is fixed to the surface of the aforementioned base members 14 by means of an adhesive agent 15, such as hot-melt adhesive agent or the like. A medium member 16 is inserted between the back side of the woven fabric sheet 13 comprising the aforementioned the other sheet Sf and the base members 14. In the example illustrated in the diagram, the medium member is thread, e.g., blended thread of cotton fibers 40%, polyester fibers 20%, and acrylic fibers 40%. Or, the thread may be 100% polypropylene fibers. The thickness of the thread is around 2,400 denier, for example.

As shown in FIG. 3, the aforementioned medium members 16 is provided singularly or in a plurality in the direction in which the main filaments 13a of the warp knitting woven fabric sheet 13 extend, and the aforementioned medium members 16 is also adhered when adhesion of the woven fabric sheet 13 and the base member 14 is performed by means of the adhesive agent 15.

The results of measurement made with a thickness meter regarding the weighted thickness of the thread around 2,400 denier used for the medium members 16 in the present invention are as follows. With the weight placed upon the thread at 0.5 g/cm2, the thickness for the blended thread of cotton fibers 40%, polyester fibers 20%, and acrylic fibers 40%, was 1.5 mm. The thickness for the thread of 100% polypropylene fibers was 1.0 mm. With the weight placed upon the thread at 50 g/cm2, the thickness for the blended thread of cotton fibers 40%, polyester fibers 20%, and acrylic fibers 40%, was 0.7 mm. The thickness for the thread of 100% polypropylene fibers was 0.5 mm.

Next are shown the measurement results using the same thickness meter for the medium member 16 comprising (using) aforementioned thread of around 2400 denier, in the event that said medium member 16 provided adhered with the adhesive agent 15 between the base member 14 of the outer cover of the disposable diaper and woven fabric sheet 13 with basic weight of 30 g/cm2 to 80 g/m2 (shown in FIG. 1 and FIG. 2). With the weight placed upon the woven fabric sheet 13 at 0.5 g/m2, the thickness H for the raised portion was H=0.2 mm when the blended thread of cotton fibers 40%, polyester fibers 20%, and acrylic fibers 40%, was used as the medium members 16, and was H=0.1 mm when the thread of 100% polypropylene fibers was used as the medium members 16. The thickness H represents the raised height of the raised portion, and is calculated by subtracting the total thickness dimensions of the base member 14, adhesive agent 15, and woven fabric sheet 13, from the total thickness dimensions of the base member 14, medium members 16, adhesive agent 15, and woven fabric sheet 13.

The apparent thread width W of one strand of the medium members 16 fixed between the base member 14 and the woven fabric sheet 13 under no weight pressure applied is as follows. The width W of the blended thread of cotton fibers 40%, polyester fibers 20%, and acrylic fibers 40%, used for the medium members 16, was 0.5 to 1.0 mm. The width W of the thread of 100% polypropylene fibers was 1.0 to 2.0 mm.

The height dimensions h of the retaining head 12a of the protrusions 12 on the one sheet Sm was set at 0.1 mm.

With the present invention, the medium members 16 are provided between the woven fabric sheet 13 and the base member 14, thus forming raised portions in the woven fabric sheet 13 which is the other sheet Sf, whereby the raised portions make it easier for the retaining heads 12a of the one sheet Sm to hook to the main filaments of the woven fabric sheet 13 or the fine filaments 13b thereof. As such, it is desirable that the thickness H of the woven fabric sheet 13 of the other sheet Sf be greater than the height dimensions h of the retaining heads 12a, in order to raise the probability of ease of hooking (retaining). In other words, in the event that the height dimensions h of the retaining heads 12a is 0.1 mm as described above, it is preferable that the thickness H of the raised portions of the other sheet Sf be 0.1 mm or greater when measured under weight of around 0.5 g/cm2.

With the retaining fastener of the above-described construction, the medium members 16 are provided between the woven fabric sheet 13 and the base member 14 of the other sheet Sf, thus forming raised portions of H in thickness in the woven fabric sheet 13. The raised portions of woven fabric sheet 13 comprise an apex (a) and inclined portions (b) on either side of the said apex (a), wherein the density of the woven fabric sheet 13 become coarse and gaps between fine filaments 13b spread at the inclined portions (b) by means of the woven fabric sheet 13 being bent.

When the one sheet Sm is brought into contact with the other sheet Sf and pressure is applied thereto, the retaining heads 12a at the tip of the protrusions 12 of the one sheet Sm enter in between the fine filaments 13b of the woven fabric sheet 13 comprising the other sheet Sf, whereby the fine filaments 13b are hooked onto the base portion of the retaining heads 12a, thus retaining the other sheet Sf and the one sheet Sm so as not to separate. Now, since the other sheet Sf are coarse at the aforementioned inclined portions (b), the retaining heads 12a enter thereto readily. Also, since the fine filaments 13b are extending at an angle inclined regarding the axial direction of the protrusions 12 at the inclined portions (b), the fibers are readily hook ed to the base portion of the retaining heads 12a.

With retaining fasteners of this type, not all of the retaining heads 12a of the one sheet Sm engage the fibers of the other sheet Sf by hooking, and even for those which have hooked, the degree of hooking, i.e., the retaining strength differs from one retaining head 12a to another. Facilitating entering of the retaining heads 12a into between the fine filaments 13b of the other sheet Sf and raising the probability of secure hooking to the fine filaments 13b thereof increases the retaining strength between the one sheet Sm and the other sheet Sf. With the retaining fastener according to the present invention, the retaining heads 12a easily enter between the fine filaments 13b of the aforementioned inclined portions (b) of the raised portion, and the fine filaments 13b are easily hook to the base portion of the retaining heads 12a, so that the retaining strength between the one sheet Sm and the other sheet Sf is increased at the aforementioned inclined portions (b). Also, regarding the portions at which the medium member 16 is not provided and a raised portion is not formed, retaining heads 12a and the fine filaments 13b are hooked at a probability equal to that of known items. Accordingly, the overall retaining strength of the retaining fastener can be increased by the area to which the aforementioned inclined portions (b) are formed.

Also, in order to retain the retaining heads 12a and fine filaments more easily at the inclined portions (b), it is preferable that the thickness H of the other sheet Sf be greater than the height dimensions h of the retaining heads 12a when the one sheet Sm and the other sheet Sf are brought into contact and pressure is applied thereto. In other words, ease of entering of the retaining heads 12a to the inclined portions (b) are facilitated by means of making the aforementioned thickness H to be greater than the height dimensions h of the retaining heads 12a.

Also, as shown in FIG. 1 thorough FIG. 3, it is preferable that the medium members 16 used for forming the raised portions on the other sheet Sf be such that extends in a direct line, such as thread. By means of using thread as the medium members 16, as shown in FIG. 1, the inclined portions (b) extend for a long distance in a direct line, wherein retaining heads 12a and woven fabric sheet 13 are hooked each other along the entire range of this direct line, consequently increasing the overall retaining strength.

Also, with the one sheet Sm and the other sheet Sf are in a state of contact, with X denoting the direction in which shearing force operates to the sheets (the direction in which the shearing force easily acts), it is preferable that the direction in which the aforementioned medium members 16 and the direction in which the inclined portions (b) extend are in a direction at right angles with the aforementioned X direction (this direction denoted by Y). By means of making the inclined portions (b) to extend in above mentioned direction, resistance effectively acts regarding the shearing force, over the entirety of the inclined portions (b).

Also, increasing the number of the medium members 16, so as to provide a plurality of medium members 16 in a parallel manner increases the area of the inclined portions (b), thus increasing the retaining strength of the one sheet Sm and the other sheet Sf. However, increasing the area too much causes the distance between the thread-like medium members 16 to be too narrow, and the effective area of the aforementioned inclined portions (b) at which the retaining heads 12a hook decreases. Accordingly, it is preferable that the ratio of the apparent area of the plurality of medium members 16 as to the total area of contact between the one sheet Sm and the other sheet Sf be between 3% to 50%. Also, it is preferable that the ratio of the apparent thread width W of one strand of the medium members 16 as to the opposing portion of the contact area of two sheets be between 3% to 15%.

FIG. 4 illustrates a disposable diaper 20 as an example of a product using the aforementioned retaining fastener. This disposable diaper 20 is a so-called "open-type" diaper, a front part 21 and rear part 22 being formed integrally. This diaper 20 is formed of a layers structure wherein absorbent material of such as a mixture of crushed pulp and absorbent polymer is provided between an inner sheet and an outer sheet. The aforementioned inner sheet is comprised of a liquid permeable non-woven fabric or the like, and the outer sheet is comprised of a resin film which is non-permeable to liquid and porous to air. In use, the rear part 22 of the diaper 20 is applied to the baby's rump and the middle part 23 is passed across the crotch and the diaper 20 is then folded in two so that the front part 21 is applied to the abdomen.

The other sheet Sf is provided to the surface of the outer sheet of the front part 21 which is applied to the abdomen. As illustrated in FIG. 1 and FIG. 2, the woven fabric sheet 13 is fixed to the surface of the outer sheet (base member 14) by means of the adhesive agent 15, wherein thread-shaped medium members 16 are provided two each to the symmetrical positions (i), (ii), and (iii), with a total of 3 raised portions each of a pair of strands being formed to either side of the woven fabric sheet 13. Also, a pair of wing-like formations 22a and 22a integrally protrude from the sides of the rear part 22, and the one sheet Sm is fixed to these wing-like formations 22a.

As described above, the wing-like formations 22a and 22a are overlapped with the front part 21 in the state that the rear part 22 is applied to the baby's rump and the front part 21 is applied to the abdomen. Then, the one sheet Sm is pressed against the other sheet Sf, causing the sheets to be retained one to another. Raised portions comprising two each are provided to the three symmetrical positions (i), (ii), and (iii), being formed to either side of the other sheet Sf, and when said one sheet contact with said the other sheet Sf, the user makes sure that at least two strands of the raised portions are contained with in the contact area. Accordingly, the one sheet Sm is contacted with the other sheet Sf at one of the positions (i), (ii), or (iii), according to the size of the body and legs of the baby, the user makes sure that at least two strands of the raised portions are contained with in the contact area. Thus, increased retaining strength at the aforementioned inclined portions (b) can be expected whether the one sheet Sm is applied to the position (i), (ii), or (iii).

Also, according to the diaper shown in FIG. 4, when the one sheet Sm and the other sheet Sf are brought into contact, the direction in which shearing force operates to the sheets is denoted by X. The direct line direction of the raised portions in which the thread-shaped medium members 16 are formed is in a Y direction which is at right angles with the X direction of the aforementioned shearing force acting, thus the retaining fastener exhibiting sufficient resistance to the shearing force at the inclined portions (b) of the raised portions, making it difficult for the one sheet Sm to come loose during usage, and also not allowing to shift easily.

As described above, according to the present invention, the retaining strength of the retaining fastener comprised of the other sheet and one sheet can be improved over known retaining fasteners, and for example, when applied to diapers, peeling away of the one sheet and the other sheet do not occur easily, nor does shift occur easily, and shifting of the diaper after it has been applied to the baby can be prevented. Example A one sheet was formed of polypropylene fibers as shown in FIG. 2, provided with retaining heads 12a having height dimensions of h=0.1±0.02 mm, the arraying pitch of the protrusions 12 being approximately 0.5 mm.

Used for the woven fabric sheet 13 comprising the other sheet Sf was tricot knitting of polyester fibers with basic weight of 30 g/m2 to 80 g/m2. Used for the medium member 16 was blended thread of cotton fibers 40%, polyester fibers 20%, and acrylic fibers 40%, this thread being around 2,400 denier. The weighted thickness of this thread was 1.5 mm at a weight of 0.5 g/cm2, and 0.7 mm at a weight of 50 g/cm2. Two pieces of this medium members 16 were used.

Two threads were used as the medium members 16, and the woven fabric sheet 13 (30×50 mm) and the medium members 16 were fixed to the base member (resin film) 14 by means of an adhesive agent 15. The thickness H (see FIG. 2) when a weight of 0.5 g/cm2 was applied to this sheet was 0.2 mm. The ratio of the total apparent area of the two strands of medium members 16 as to the opposing area of the one sheet and the other sheet was 7%.

The one sheet Sm and the other sheet Sf combined using the aforementioned two strands of medium members 16 thus formed an embodiment of the present invention. A comparative example was also fabricated, not using the aforementioned thread medium members 16, but adhering the woven fabric sheet 13 which is the other sheet Sf to the fine filaments 14 over the entire area with the adhesive agent 15, and combining said the other sheet Sf and the one sheet Sm. Testing to measure peeling strength, based on JIS K6854 stipulations was performed to both the above embodiment and the comparative example.

(Testing Method)

Figure 5:
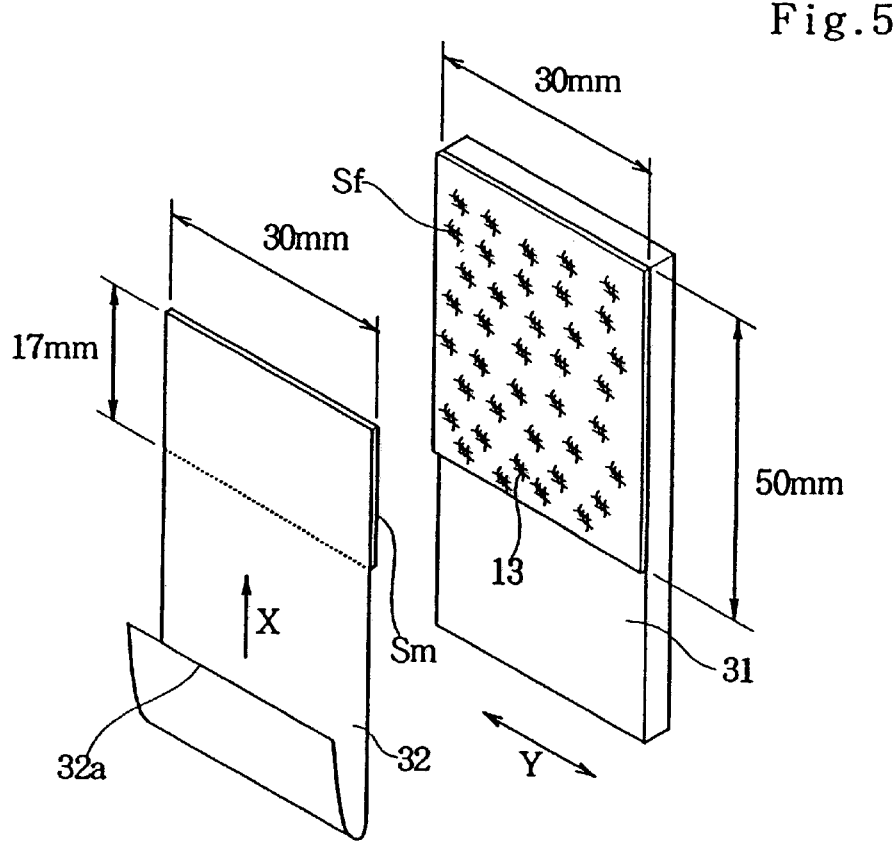
FIG. 5 is a perspective view describing a method of performing peeling test of the retaining fastener.

FIG. 5 is a perspective view of the one sheet and the other sheet used in this test. A 30×50 mm piece of the other sheet Sf of the present embodiment having two strands of medium members 16 between the woven fabric sheet 13 and the fine filaments 14, and a 30×50 mm piece of the other sheet of the comparative example not comprising the medium members 16 were fixed to the surface of an acrylic plate 31 using double-sided adhesive tape. The linear direction of the two strands of the medium members 16 in the present embodiment was set so as to be in the Y direction which intersects the direction at which shearing force from peeling occurs (X direction) at right angles.

Figure 6:
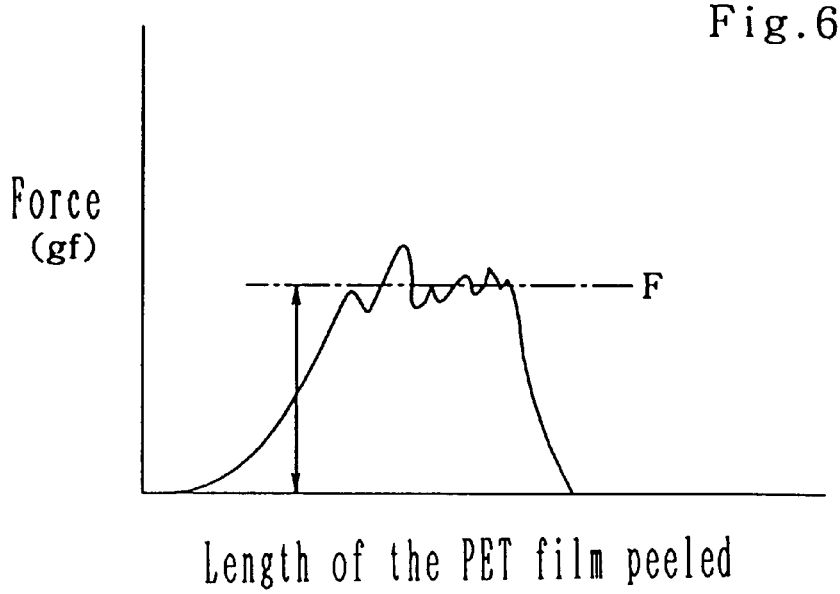
FIG. 6 is a linear graph showing the measurement values of the peeling test.
Figure 7:
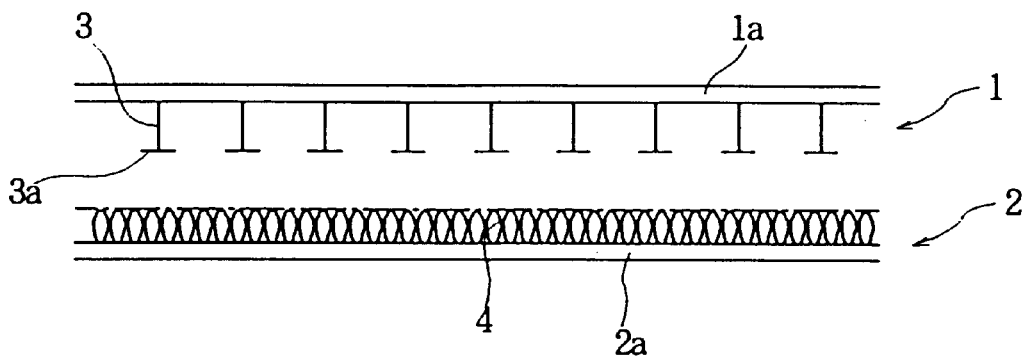
FIG. 7 is a cross-sectional diagram illustrating the structure of a retaining fastener for a prior art.

The one sheet Sm was made to be 30×17 mm in size, and adhered to polyethylenetelephtalate (PET) film 32 using double-sided adhesive tape. The one sheet Sm was brought into contact with the other sheet Sf, the roller was operated for one reciprocal round from the surface of the PET film 32 at a force of 700 gf, thus retaining the one sheet Sm and the other sheet Sf. Subsequently, the base edge 32a of the PET film 32 was held by the chuck of the tensile tester, and peeling was performed at a peeling angle 180° to the surface of the acrylic plate 31 at a peeling speed of 300 mm/min. The change in force measure at this time by the tensile tested is illustrated in FIG. 6. The average of the fluctuation near the maximum value of this force is the peeling strength F.

(Test Results)

As results of the measurement test, it was found that the peeling strength F of the present embodiment was 151 gf, and that of the comparative example was 105 gf. As can be understood from this, increase in peeling strength could be clearly confirmed as a result of causing partial rising of the woven fabric sheet 13 of the other sheet Sf using a medium members 16.

What is claimed is:

1. A retaining fastener comprising a hook sheet and a loop sheet which can be repeatedly attached together and detached from each other, wherein;

a plurality of protrusions having retaining heads are provided on the hook sheet, and the retaining heads are for being caught in the loop sheet, and a plurality of linear medium members are provided intermittently between the loop sheet and a base member to raise portions of the loop sheet toward the hook sheet so that inclined portions are provided in the raised portions of the loop sheet facing the hook sheet and wherein each of said plurality of linear medium members is a thread made of fibers.

2. A retaining fastener according to claim 1, wherein a height of the raised portions of the loop sheet is greater than a thickness of the retaining heads of the protrusions.

3. A retaining fastener according to claim 1, wherein the loop sheet is a warp-knit which is kitted from two or more kinds of filaments, and at least one kind of the filaments is a multifilament formed by twisting a plurality of fine filaments or fibers, the fine filaments or fibers being fluffy and protruding from the multifilament.

4. A retaining fastener according to claim 3, wherein the multifilaments extend in a zigzag manner.

5. A diaper made of a layered member comprising a covering sheet, an inner sheet having liquid permeability, and an absorbent material provided between the two sheets, wherein:

the layered member has a rear part which is to be applied to a rump of a wearer, a middle part which is to be passed across a crotch thereof, and a front part which is to be applied to an abdomen thereof in order, and the rear part and the front part are partially overlapped and attached together by means of a retaining fastener to form a pants-shape to be applied to the wearer, the retaining fastener comprises a hook sheet and a loop sheet which can be repeatedly attached together and detached from each other, and the loop sheet is fixed to the rear part or the front part, a plurality of protrusions having retaining heads are provided on the hook sheet, and the retaining heads are for being caught in the loop sheet, and a plurality of threads made of fibers are provided intermittently between the loop sheet and the rear part or the front part to raise portions of the loop sheet toward the hook sheet so that inclined portions are provided in the raised portions of the loop sheet, and wherein the plurality of threads are provided extending in a direction toward the middle part of the layered member and having intrevrals between each other in a direction of a waist line of the wearer to which the diaper is to be applied.

6. A diaper according to claim 5, wherein a height of the raised portions of the loop sheet is greater than a thickness of the retaining heads of the protrusions.

7. A diaper according to claim 5, wherein the loop sheet is a warp-knit which is knitted from two or more kinds of filaments, and at least one kind of the filaments is a multifilament formed by twisting a plurality of fine filaments or fibers, the fine filaments or fibers being fluffy and protruding from the multifilament.

8. A diaper according to claim 7, wherein the multifilaments extend in a zigzag manner.

* * * * *